US012754107B2

(12) United States Patent
Oertli et al.

(10) Patent No.: US 12,754,107 B2
(45) Date of Patent: Oct. 6, 2026

(54) SAMPLE TAKING DEVICE, SAMPLE TAKING SYSTEM AND METHOD OF OPERATING A SAMPLE TAKING DEVICE

(71) Applicant: LockCon AG, Wil (CH)

(72) Inventors: Christian Oertli, Oberhelfenschwil (CH); Monika Egli, Wil (CH)

(73) Assignee: LockCon AG, Wil (CH)

( * ) Notice: Subject to any disclaimer, the term of this patent is extended or adjusted under 35 U.S.C. 154(b) by 281 days.

(21) Appl. No.: 18/599,716

(22) Filed: Mar. 8, 2024

(65) Prior Publication Data

US 2024/0302249 A1 Sep. 12, 2024

(30) Foreign Application Priority Data

Mar. 10, 2023 (DE) ..................... 10 2023 106 084.8
May 16, 2023 (DE) ..................... 10 2023 112 897.3

(51) Int. Cl.

| | |
|---|---|
| ***G01N 1/14*** | (2006.01) |
| ***B01L 3/00*** | (2006.01) |
| ***B01L 3/02*** | (2006.01) |
| ***B01L 9/00*** | (2006.01) |
| ***G01N 1/00*** | (2006.01) |

(Continued)

(52) U.S. Cl.

CPC .............. *G01N 1/14* (2013.01); *B01L 3/0262* (2013.01); *B01L 3/502715* (2013.01); *G01N 1/2035* (2013.01); *G01N 1/2813* (2013.01); *G01N 33/49* (2013.01); *B01L 3/5023* (2013.01); *B01L 9/52* (2013.01); *B01L 2300/043* (2013.01); *B01L 2300/0816* (2013.01); *B01L 2300/0887* (2013.01); *B01L 2300/126* (2013.01); *G01N 2001/002* (2013.01); *G01N 2001/1436* (2013.01); *G01N 2001/205* (2013.01)

(58) Field of Classification Search

CPC ...... G01N 1/14; G01N 1/2035; G01N 1/2813; G01N 33/49; G01N 2001/002; G01N 2001/1436; G01N 2001/205; B01L 3/0262; B01L 3/502715; B01L 3/5023; B01L 9/52; B01L 2300/043; B01L 2300/0816; B01L 2300/0887; B01L 2300/126

See application file for complete search history.

(56) References Cited

U.S. PATENT DOCUMENTS 6,272,939 B1 * 8/2001 Frye .................... B01L 3/50853 73/864.81
11,052,397 B2 * 7/2021 Triva ................. A61B 10/0045

(Continued)

FOREIGN PATENT DOCUMENTS

CN 203101395 U 7/2013
CN 103983795 A 8/2014

(Continued)

OTHER PUBLICATIONS

EP-0692097-B1, English Translation (Year: 1999).*

(Continued)

*Primary Examiner* — Ryan D Walsh
(74) *Attorney, Agent, or Firm* — Posz Law Group, PLC

(57) ABSTRACT

A sample taking device has an applicator unit for an application of a liquid sample to a first sample card, the applicator unit is in an application state configured for a simultaneous application of the liquid sample to a second sample card.

17 Claims, 8 Drawing Sheets

(51) Int. Cl.

| | |
|---|---|
| ***G01N 1/20*** | (2006.01) |
| ***G01N 1/28*** | (2006.01) |
| ***G01N 33/49*** | (2006.01) |

(56) References Cited

U.S. PATENT DOCUMENTS

| | | | | |
|---|---|---|---|---|
| 2004/0171173 | A1* | 9/2004 | Eckermann ........... | B01L 3/5023 436/514 |
| 2012/0058496 | A1 | 3/2012 | Katsuhara et al. | |
| 2016/0089669 | A1 | 3/2016 | Regnier et al. | |
| 2017/0102399 | A1 | 4/2017 | Mamenta | |
| 2017/0282177 | A1 | 10/2017 | Bedrio | |
| 2018/0164281 | A1 | 6/2018 | Béguin et al. | |
| 2019/0033184 | A1* | 1/2019 | Bedrio .................. | B01L 3/5023 |
| 2019/0049353 | A1 | 2/2019 | Henion et al. | |

FOREIGN PATENT DOCUMENTS

| | | | | |
|---|---|---|---|---|
| EP | 0692097 | B1 * | 3/1999 | ............. G01N 30/90 |
| JP | 2012-042310 | A | 3/2012 | |
| JP | 6864919 | B2 | 4/2021 | |

OTHER PUBLICATIONS

German Search Report mailed Oct. 11, 2023 in corresponding German Patent Application No. 10 2023 112 897.3 (and English translation).

Extended European Search Report dated Aug. 13, 2024 issued for the corresponding European Patent Application No. 24162395.8 (and English translation).

* cited by examiner

SAMPLE TAKING DEVICE, SAMPLE TAKING SYSTEM AND METHOD OF OPERATING A SAMPLE TAKING DEVICE

CROSS-REFERENCE TO RELATED APPLICATIONS

This patent application is a U.S. follow-up application of European patent application EP 24162395.8, filed on Mar. 8, 2024, which is based on and claims priority to German patent application DE 10 2023 106 084.8, filed on Mar. 10, 2023, and to German follow-up patent application DE 10 2023 112 897.3, filed on May 16, 2023, the contents of which are incorporated herein by reference.

PRIOR ART

The invention concerns a sample taking device, a sample taking system and a method of operating a sample taking device.

Devices for an application of a liquid sample to a sample card have already been proposed.

The objective of the invention is in particular to provide a generic device having improved properties with regard to sample taking efficiency. The objective is achieved according to the invention.

Advantages of the Invention

The invention is based on a sample taking device with an applicator unit for an application of a liquid sample to a first sample card.

It is proposed that the applicator unit is in an application state configured for a simultaneous application of the liquid sample to a second sample card.

Such an implementation of the sample taking device advantageously allows augmenting sample taking efficiency. In particular, a second sample spot can be created on the second sample card simultaneously to a first sample spot on the first sample card, which are then comparable to one another, in particular as they have the same liquid sample. Furthermore, the first sample card and the second sample card may be transported and/or stored separately from each other. In particular, the sample taking device may advantageously, in particular simultaneously, provide an "A" sample on the first sample card and a "B" sample on the second sample card, for example for a doping test.

The liquid sample is preferably a blood sample. The liquid sample preferably comprises blood, in particular capillary blood, said blood preferably being whole blood. Alternatively or additionally, it is conceivable that the liquid sample comprises blood serum and/or blood plasma or the like. The liquid sample may comprise further substances, for example a dilution agent or something like that. Alternatively or additionally, it would be conceivable that the liquid sample comprises a different liquid, which is in particular embodied as a body liquid.

In particular, the sample taking device is configured to provide at least the first sample spot and the second sample spot, comprising the liquid sample at least partly, on the respective sample card, and in particular to generate at least the first sample spot and the second sample spot from the liquid sample. The sample taking device is in particular configured to be used in a Dried-Blood-Spot test, wherein a respective sample spot may be further processed, in particular dried, in the Dried-Blood-Spot test, in particular to form a dried blood spot.

A "simultaneous application" is in particular to mean an application of a liquid sample, in particular to the second sample card, which is carried out at least in a same work process, preferably at least substantially at the same time, as the application of the liquid sample to the first sample card. Preferably, in the simultaneous application at least one point in time of the application of the liquid sample to the first sample card overlaps with at least one point in time of the application of the liquid sample to the second sample card. It is conceivable that the simultaneous applications take place merely at the same points in time. Principally, however, it would also be conceivable that the simultaneous applications of the liquid sample to the first sample card and to the second sample card are realized at least partly consecutively at the same time but within the same work process. In particular, in the case of simultaneous application, the first sample card and the second sample card are arranged in the sample taking device in the same work state at the same time.

The sample taking device is preferably part of a sample taking system, which in particular comprises in addition to the sample taking device the first sample card and the second sample card. The sample cards are preferably realized as, in particular customary, dry-blood cards. The first sample card and the second sample card are preferably realized identically to each other. The following description of a sample card is therefore to be read on the first and on the second sample card. The sample card preferably comprises a card base made, for example, of cardboard and/or paper. In particular, the sample card comprises at least one sample carrier, which is in particular made of filter paper and is configured for an absorption of the liquid in order to provide the sample spot. The sample carrier may be arranged in a recess of the card base that is rectangular or circle-shaped or has a different shape deemed expedient by someone skilled in the art. It is conceivable that the sample taking system comprises further units and/or elements, for example a pricking unit, which is in particular embodied as a lancet, for a puncturing of a test person for capillary blood sampling.

"Configured" is to mean designed and/or equipped. By an object being configured for a certain function is in particular to be understood that the object carries out this certain function in at least one application state and/or operation state.

It is further proposed that the sample taking device includes a card carrier unit comprising a first holder for the first sample card and a second holder for the second sample card. In this way it is advantageously possible to align the first sample card and the second sample card for the application of the liquid sample and/or to hold, in particular fix, the first sample card and the second sample card in an advantageous position during the application of the liquid sample. Preferably the first holder and the second holder are realized identically to each other. Preferably the holder fixes the sample card to the card carrier unit. Preferably a connection of the card carrier unit and the respective sample card is realized in such a way that it is separable by means of the respective second holder. The holder is configured for a holding of the sample card, preferably for a form-fit connection, in particular a plug connection and/or clamp connection, of the sample card and the card carrier unit, in particular the holder. The holder is preferably configured to accommodate at least a subregion of the sample card in a form-fit manner. This allows particularly simple attaching of the sample card, which is in particular at least partly elastically deformable, to the card carrier unit and/or removal of the sample card from the card carrier unit.

Furthermore, it is proposed that the card carrier unit includes a first card carrier element, which comprises the first holder, and a second card carrier element, which is movable relative to the first card carrier element and comprises the second holder. In this way a position of the first sample card held on the first card carrier element may advantageously be oriented with respect to a position of the second sample card held on the second card carrier element. In particular, at least a removal and/or an attachment of the first sample card and/or of the second sample card from and/or to the card carrier unit can be advantageously simplified.

The first card carrier element and the second card carrier element are preferably realized identically to each other. The respective card carrier element is preferably realized at least partially in a plate shape and in particular has a material thickness preferably corresponding to maximally 50%, preferentially no more than 20%, especially preferentially no more than 10% and particularly advantageously maximally 5% of a length and/or a width of the card carrier element, wherein the card carrier element in particular comprises mutually opposed sides having planar surfaces. The first card carrier element and/or the second card carrier element preferably—in particular in each case—comprise/s a card carrier plate element, which in particular extends along a largest side surface of the first card carrier element and/or of the second card carrier element. Preferably the sample card held on the card carrier element, in particular a largest side surface of the sample card, extends parallel to the largest side surface of the card carrier element and/or of the card carrier plate element. The sample card held on the card carrier element preferably forms a contact surface with the card carrier plate element and/or with the largest side surface of the card carrier element.

It is conceivable that the holder has an at least sectionwise overhang at a periphery, in particular a corner and/or an edge, of the card carrier plate element in which the sample card is clamped. Alternatively or additionally, it is conceivable that the holder has at least a groove and/or a gap for at least partly accommodating a peripheral region, in particular at least an edge region and/or a corner region, of the sample card. It is conceivable that the first sample card and/or the second sample card comprise/s at least one alignment-indicating feature, for example a rounded and/or cut-off corner, by which in particular an alignment of the sample card for being held at the card carrier unit is defined.

It would be conceivable that the second card carrier element is linearly and/or freely movable relative to the second card carrier element. In an advantageous implementation of the card carrier unit, it is however proposed that the second carrier element is pivotable relative to the first card carrier element by means of at least one hinge of the card carrier unit. This allows achieving particularly advantageous relative positions of the first card carrier element and the second card carrier element. It is conceivable that the card carrier unit comprises more than one hinge, in particular two hinges, for a pivoting of the second card carrier element relative to the first card carrier element. Alternatively, it would be conceivable that the second card carrier element is immobile relative to the first card carrier element.

Moreover, it is proposed that the first card carrier element and the second card carrier element are fixedly connected to each other. In this way it is advantageously possible to reduce a complexity of the card carrier unit and/or to increase an operator's comfort, in particular as a number of loose components of the card carrier unit is advantageously reducible. In particular, the first card carrier element and the second card carrier element are fixedly connected to each other via the hinge. The fix connection is in particular a connection that is at least partly non-separable, in particular non-separable by the operator, and/or a connection that is in particular present in each operation state of the sample taking device. The hinge is preferably arranged in each case on a longest edge of the first card carrier element and/or of the second card carrier element, said longest edges being in particular realized identically to each other, and is in particular connected to the respective longest edge. The hinge is in particular arranged in each case on the card carrier plate element of the first card carrier element and/or of the second card carrier element, and is in particular connected to the respective card carrier plate element. The pivoting preferably includes a rotation axis parallel to the longest edge of the first card carrier element and/or of the second card carrier element.

It would be conceivable that the hinge is, in particular in each case, connected to the first card carrier element and/or the second card carrier element via a gluing connection and/or screw connection and/or plug connection and/or the like. Preferably the first card carrier element and the second card carrier element are connected to each other in a one-part implementation. This in particular allows especially advantageous reducing a complexity of the card carrier unit and/or increasing production efficiency. "In a one-part implementation" is in particular to mean formed in one piece. Preferably this one piece is produced from a single blank, a mass and/or a cast, particularly preferentially in an injection-molding procedure, in particular a one-component and/or multi-component injection-molding procedure. The hinge is preferably realized as a film hinge. In particular, the hinge is connected to the first card-carrier element and/or the second card carrier element in a one-part implementation. Preferably the card carrier unit is realized completely in a one-part implementation. Preferably the first card carrier element and the second card carrier element are connected to each other merely via the hinge, in a one-part implementation. Alternatively or additionally, it is conceivable that the first card carrier element is connected to the second card carrier element via the applicator unit. It is in particular conceivable that the first card carrier element is connected to the applicator unit via at least one first hinge and/or that the second card carrier element is connected to the applicator unit via at least one second hinge. The card carrier unit preferably comprises at least one synthetic material and is in particular made of a synthetic material. The card carrier unit may be realized so as to be transparent or at least partly opaque.

It is further proposed that the applicator unit is, at least in the application state, connected to the card carrier unit, such that it is in particular possible to apply a liquid sample, advantageously from the applicator unit, to the sample card held in the respective card carrier unit. Preferably the applicator unit and the card carrier unit are connected to each other so as to be immobile relative to each other, at least in the application state. Advantageously, an especially stable application and/or particularly precise application, in particular to the sample carrier of the first sample card and/or of the second sample card, can be provided.

Beyond this it is proposed that the applicator unit is in the application state arranged at least partly between the first card carrier element and the second card carrier element. In this way, the sample taking device can be provided in an especially compact manner for the simultaneous application of the liquid sample to the first sample card and the second sample card. In particular, at least in the application state, the first sample card is arranged at least partly between the applicator unit and the first card carrier element. In particular, at least in the application state, the second sample card is arranged at least partly between the applicator unit and the second card carrier element. In particular, the first card carrier element is arranged on a side of the applicator unit that is situated opposite an arrangement of the second card carrier element. Preferably, in the application state, the applicator unit, the first card carrier plate element and the second card carrier plate element are arranged parallel to one another. In particular, the largest side surfaces of the applicator unit, of the first card carrier element and of the second card carrier element extend parallel to one another. The applicator unit is in the application state preferably arranged at least largely between the first card carrier element and the second card carrier element, wherein in particular at least 55%, advantageously at least 65%, preferably at least 75%, especially preferentially at least 85% and especially advantageously at least 90% of a volume and/or of a mass of the applicator unit are arranged between the first card carrier element and the second card carrier element.

Preferably the card carrier unit is pivotable, in particular relative to the applicator unit, at least between the sampling state and the application state.

It is also proposed that the sample taking device comprises a fixing unit, which prevents the applicator unit from slipping out of the card carrier unit. In this way the applicator unit can be connected to the card carrier unit in an advantageously stable manner. It is in particular advantageously possible, in the application state, to avoid a slipping of the applicator unit relative to the first sample card and/or the second sample card held on the applicator unit.

The fixing unit preferably forms a form-fit connection, in particular a clamp or snap connection, between the applicator unit and the card carrier unit. The fixing unit preferably comprises at least one applicator holding element, in particular four identically realized applicator holding elements, at the applicator unit. The applicator holding element is preferably part of the applicator unit. The applicator holding element preferably forms at least one support surface for holding the applicator unit. The fixing unit preferably has a peripheral region of the card carrier unit, in particular of a card carrier element, which is accommodated in the applicator holding element. The applicator holding element preferably has a kink for accommodating the peripheral region of the card carrier unit. The kink may in particular have an angle of at least substantially 90 degrees, said angle deviating from a 90-degree angle in particular by less than 20 degrees, preferably by less than 10 degrees and especially preferentially by less than 5 degrees. It is conceivable, in particular at least for simplified insertion and/or removal of the card carrier unit and/or for the pivoting, that the applicator holding element is realized so as to be at least partly elastic and/or foldable. It is conceivable that the applicator holding element delimits and/or prevents a pivoting of the second card carrier element relative to the first card carrier element in the application state. Alternatively or additionally, it is conceivable that the fixing unit is realized integrally with the hinge.

The applicator unit is connected to the card carrier unit by means of the fixing unit, in particular in an assembled state. Preferably the assembled state comprises at least the application state and in particular a sampling state.

Furthermore, it is proposed that the sample taking device comprises a closing unit, which fixes a relative position of the first card carrier element with respect to the second card carrier element in the application state. This allows providing an advantageous and in particular stable position of the sample cards in the application state.

The closing unit preferably forms a form-fit connection, for example a clamp connection and/or advantageously a snap connection, between the applicator unit and the card carrier unit and/or between the first card carrier element and the second card carrier element. The closing unit preferably comprises at least one closing element, preferably four identically realized closing elements, at the applicator unit. The closing element is preferably part of the applicator unit. The closing element preferably has at least one recess, which is in particular configured, for a fixing of the relative position of the first card carrier element with respect to the second carrier element in the application state, to at least partly accommodate the counter closing element. Preferably the closing element exerts in the application state a force along a pivoting direction of the card carrier element onto the counter closing element. Preferably, for the snap connection the closing element and the counter closing element are realized so as to be at least partly elastic. The counter closing element is preferably part of the card carrier unit. Advantageously, the counter closing element may be realized as an unevenness on the card carrier element, in particular at an edge of the card carrier element. Alternatively it is conceivable that the closing element and the counter closing element are part of the card carrier unit wherein, for a fixing of the relative position of the first card carrier element with respect to the second card carrier element in the application state, the closing element and the counter closing element are in particular respectively arranged on the first card carrier element and the second card carrier element.

Preferably, the applicator unit is at least in the application state connected to the card carrier unit, in particular in an immobile manner, by means of the fixing unit and/or of the closing unit. In particular, the first card carrier element and the second card carrier element and the applicator unit are fixed relative to one another by means of the fixing unit and the closing unit.

It is moreover proposed that the applicator unit comprises a first applicator element for an application of the liquid sample to the first sample card, and comprises a second applicator element for an application of the liquid sample to the second sample card, the first applicator element and the second applicator element being connected via a separating unit of the applicator unit. In this way, simultaneous application of the liquid sample to the first sample card and the second sample card can be provided in a particularly effective manner. Furthermore, the applicator unit and/or the sample taking device may be realized in an especially compact manner and/or a production efficiency of the applicator unit and/or the sample taking device can be advantageously augmented.

A respective applicator element preferably comprises at least the applicator holding element and/or the closing element and/or an applicator plate element. In particular, the applicator element is realized at least partly in a plate-like manner.

The applicator holding element is preferably connected to the applicator plate element. The applicator holding element may be connected to the applicator plate element by means of a screw connection and/or adhesive connection and/or plug connection or the like. The applicator holding element is preferably arranged on a side of the applicator plate element that is situated opposite the separating unit.

The closing element is preferably connected to the applicator plate element. The closing element may be connected to the applicator plate element via a screw connection and/or adhesive connection and/or plug connection or the like. The closing element is preferably connected to the applicator plate element in a one-part implementation. The closing element preferably extends above a side of the applicator plate element that is situated opposite the separating unit. The closing element is preferably arranged on an upper side of the applicator plate element, in particular with respect to the orientation of the sample taking device at least in the application state. The closing element is preferably arranged at the applicator plate element above the applicator holding element. The closing element and the applicator holding element preferably have surfaces parallel to each other, which in particular extend perpendicularly to the largest side surface of the applicator element.

Preferably the applicator unit comprises a connection between a largest side surface of the first applicator element and a largest side surface of a second applicator element. In particular, the first applicator plate element is connected to the second applicator plate element.

The separating unit in particular comprises at least one partial surface of a side surface of the first and/or of the second applicator element which is configured for a connection. The separating unit is preferably embodied as a film unit, which in particular comprises at least one film. The film unit may comprise more than one film, which may in particular be arranged at least partly upon one another or offset from one another, between the first applicator element and the second applicator element. The film may preferably be realized as a gluing film, in particular having a one-faced and/or double-faced gluing agent. Alternatively, the film may be realized, for example, as an adhesive film or as a sticking film or the like.

Alternatively, in particular additionally, it is conceivable that the first applicator element and the second applicator element are connected by means of a different connection mechanism. It is in particular conceivable that the first applicator element and the second applicator element are connected at least via a form-fit and/or friction-fit connection, in particular via at least one plug connection. Preferably the first applicator element and the second applicator element have at least one recess and/or at least one plugging element for creating the plug connection, wherein the recess of the first applicator element is in particular configured for receiving a plugging element of the second applicator element, and/or the plugging element of the first applicator element is in particular configured to be received in the recess of the second applicator element. Alternatively or additionally, it would be conceivable that the applicator unit comprises a different connection of the first applicator element and the second applicator element, for example a screw connection and/or a welding connection and/or a different connection that is deemed expedient by someone skilled in the art.

It is further proposed that the first applicator element comprises at least one first flow channel and the second applicator element comprises at least one second flow channel, the first flow channel and the second flow channel being at least partly closed by means of the separating unit. In this way the simultaneous application of the liquid sample can be provided in a particularly advantageous manner. In particular, production efficiency is advantageously augmentable, in particular with regard to a formation of the flow channels.

The first flow channel and the second flow channel are realized so as to be identical to each other in the first applicator element and the second applicator element. The first flow channel and/or the second flow channel are/is preferably realized as a milled-out portion in the first applicator element and/or the second applicator element, in particular in the first applicator plate element and/or the second applicator plate element, said milled-out portion/s being at least partly closed by the separating unit, in particular the film unit. In particular, the first flow channel and the second flow channel are closed by the separating unit along a longitudinal extension direction of the respective flow channel. In an implementation of the film unit as at least one gluing film, it is conceivable that the gluing film comprises a recess of the gluing agent, at least in a region of the first flow channel and/or the second flow channel, which in particular advantageously allows avoiding and/or reducing a contamination of the first flow channel and/or of the second flow channel.

The first flow channel and the second flow channel are in particular configured at least for a transport of the liquid sample for the application to the first card carrier unit, respectively the second card carrier unit. This advantageously allows increasing operating comfort, in particular as a liquid source, for example a pricked finger or the like, does not have to be laid upon the sample card directly. It is in particular advantageously possible to make the sample taking device available for home use. The first flow channel and/or the second flow channel, in particular respectively, have/has a channel entry and/or a channel exit. The channel entry is in particular configured for receiving the liquid sample. In particular, the channel entry may be configured for the liquid source of the liquid sample to be laid thereon. The first flow channel and/or the second flow channel in each case in particular have/has a channel exit which is in a correct positioning of the sample taking device, in particular at least with respect to a gravity direction, in the receiving state and/or the application state, arranged below the channel entry. In this way the liquid sample can be transported, in particular at least partly by means of gravity, from the channel entry to the channel exit. The channel entry is preferably arranged at an upper side edge of the applicator element. In the applicator unit, the channel entry of the first flow channel and the channel entry of the second channel entry are preferably configured for simultaneous taking-out of the liquid sample from the liquid source. Preferably the channel entry of the first flow channel and the channel entry of the second flow channel are spaced apart from each other merely by the separating unit, in particular merely by the film unit, as a result of which an especially advantageous simultaneous accommodation of the liquid sample in the first flow channel and the second flow channel can be provided. The first flow channel and/or the second flow channel are preferably realized as capillaries/is preferably realized as a capillary, wherein the liquid sample is in particular transported from the channel entry to the channel exit at least partly via a capillary effect. The channel exit may comprise a tapering of a diameter of the flow channel, by which in particular outflow of the liquid sample outside the application state is advantageously avoidable. In the application state the channel exit is preferably in contact with the sample carrier of the respective sample card, wherein the liquid sample can be transported from the channel exit to the sample carrier at least partly via a suction performance of the sample carrier. The channel exit of the first flow channel is preferably arranged on an, in particular largest, side surface of the applicator unit that is situated opposite the channel exit of the second flow channel. The channel exit is preferably formed in a bulge of the applicator element, in particular of the applicator plate element, such that in particular a contact of the channel exit and the sample card, in particular the sample carrier, can be provided in a reliable manner.

The first flow channel and/or the second flow channel are/is preferably realized so as to be volumetric, wherein in particular a quantified volume of the first flow channel and/or a quantified volume of the second flow channel, which are/is filled with the liquid sample, are/is applied to the first sample card and/or to the second sample card. Preferably the first flow channel and/or the second flow channel are/is configured for storing the liquid sample until reaching the application state. Preferably the first flow channel and/or the second flow channel are/is configured to be filled completely and/or until a mark has been reached. It is conceivable that the applicator unit is realized at least partly in a transparent manner, by which the filling of the first flow channel and/or the second flow channel by the operator can be advantageously simplified. Preferably the first flow channel and/or the second flow channel have a volume of at least 5 μL, preferably at least 10 μL, particularly preferably at least 15 μL, and/or of maximally 40 μL, preferably no more than 30 μL, particularly preferably no more than 25 μL. Especially advantageously the first flow channel and/or the second flow channel have a volume of precisely 20 μL. Preferably the first flow channel and the second flow channel have a same volume. The first flow channel and/or the second flow channel are/is in particular realized in a curved fashion, wherein an advantageous volume of the first flow channel and/or of the second flow channel as well as a particularly compact implementation of the applicator unit can be provided. In particular, it is advantageously possible to avoid or reduce outflow of the liquid sample from the first flow channel and/or the second flow channel outside the application state.

Preferably the first applicator element and/or the second applicator element comprise/comprises at least one further first flow channel and/or at least one further second flow channel. This advantageously allows further increasing sampling efficiency, and in particular providing more than one sample spot on the first sample card and/or the second sample card. For example, the first applicator element and/or the second applicator element may, in particular in each case, comprise precisely three flow channels. Preferably all flow channels of the applicator unit have respectively identical volumes. In the applicator unit, the channel entry of the flow channel and a channel entry of the further flow channel of the respective applicator element are preferably configured for simultaneous taking-out of the liquid sample from the liquid source.

Furthermore, it is proposed that the first applicator element and the second applicator element are realized identically to each other. This in particular allows advantageously augmenting production efficiency of the applicator unit. Preferably opposing sides of the first applicator element and of the second applicator element, which is connected to the first applicator element in the applicator unit, are realized identically to each other. The first applicator element and the second applicator element preferably comprise at least one synthetic material and may in particular be made of a synthetic material. Alternatively, it would be conceivable that the first applicator element and the second applicator element are realized so as to be at least partly different from each other, for example mirror-symmetrical to each other.

In one aspect of the invention, which may be considered on its own or in combination with further aspects of the invention, it is proposed that the sample taking device comprises a transport unit, which is connectable with the applicator unit for a transfer of the liquid sample to the applicator unit. In this way particularly effective and/or simple and/or secure liquid sample taking, in particular blood sampling, is achievable. Advantageously the liquid sample can be taken at the liquid source in an especially simple and/or effective manner, and can in particular be fed into the applicator unit in a particularly secure manner. Furthermore, it is advantageously possible to provide a liquid sample taking in a body region in which liquid sample taking by direct contact with the applicator unit is in particular especially difficult to realize, for example at an arm and/or foot and/or the like. Moreover, the liquid sample can be taken from the liquid source and fed into the applicator unit in an advantageously temporally offset manner.

The transport unit is in particular configured for a transport of the liquid sample between the liquid source and the applicator unit. The transport unit in particular comprises a receiving region for receiving the liquid sample. At least for transport and/or storage of the liquid sample, the receiving region is at least partly closable. Preferably the transport unit is realized at least section-wise in a tube-shaped manner and the receiving region is in particular realized at least section-wise in a cylindrical shape. Alternatively, a different shape of the transport unit and/or of the receiving region, deemed expedient by someone skilled in the art, would be conceivable. Preferably the transport unit comprises an outer body, which is in particular at least section-wise tube-shaped and which delimits the receiving region at least partly. Preferably the transport unit has, in particular on an upper side of the transport unit, a receiving opening for receiving the liquid sample from the liquid source. The transport unit preferably has, in particular below the receiving opening, at least one transfer opening for a transfer of the liquid sample to the applicator unit.

In particular, the transport unit may be realized at least partly, in particular completely, in a transparent manner in order to permit a view into the receiving region. The transport unit may furthermore comprise a volume indication, in particular a minimal-volume indication, for indicating a volume, in particular a minimal volume, of liquid in the receiving region. Particularly preferably the minimal volume may be 120 μl.

The transport unit is preferably connectable to the applicator unit in a form-fit and/or friction-fit manner. Preferentially the transport unit is connectable to the applicator unit by a plug connection. Preferably the transport unit is configured for an accommodation of the at least one channel entry of the applicator unit. Preferentially the transport unit is configured for an accommodation of all channel entries of the applicator unit. Preferably the transport unit that is connected to the applicator unit is arranged above the applicator unit at least largely, in particular by at least 55%, advantageously by at least 65%, preferably by at least 75%, particularly preferably by at least 85% and especially advantageously by at least 90% of a volume and/or a mass of the transport unit. Preferably the receiving region is arranged above the applicator unit, in particular above the at least one channel entry. This allows providing particularly simple transfer of the liquid sample from the transport unit to the applicator unit, in particular by gravity.

It is further proposed that the transport unit comprises a valve unit which is configured, during a connection of the transport unit to the applicator unit, to be pressed open by the applicator unit. This enables especially advantageous providing of a connection between the transport unit and the applicator unit for a transfer of the liquid sample. In particular, during the connection of the transport unit to the applicator unit, a connection for a liquid sample transfer can be provided, in a particularly simple manner, automatically and in particular without further steps. It is moreover possible to increase safety as the valve unit can only be opened if the transport unit is connected to the applicator unit.

The valve unit preferably comprises a valve element, which is preferentially embodied as a ball. The valve element is preferably made of metal, while a further material deemed expedient by someone skilled in the art, for example a synthetic material or the like, would also be conceivable. The valve unit preferably at least partly includes the outer body of the transport unit. Preferably the outer body, which is in particular at least section-wise tube-shaped, has at least one narrowing, in which the valve element is arranged in a closed state of the valve unit. Preferably the valve element is in the closed state of the valve unit fastened in the narrowing of the outer body in a form-fit and/or friction-fit manner and in particular closes the at least one transfer opening. Preferably, for a pressing open of the valve unit, the valve element is displaceable out of its fastened position, in particular relative to the outer body. Preferably, for a pressing open of the valve unit, a portion of the applicator unit presses directly upon the valve element. Alternatively, a different implementation of the valve unit, in particular the valve element, would be conceivable, in which the valve unit could be closed, for example, by a locking bar or the like, which is in particular pressed open during a connection of the transport unit to the applicator unit. Preferably, during a transfer of the liquid sample to the applicator unit, the pressing open is directed in a direction opposed to the flow of the liquid sample.

Preferably the valve unit can be transferred only from the closed state into a pressed-open state. Preferably the valve unit can be pressed open just once, wherein the pressed-open state of the valve unit is in particular also maintained when the transport unit has been removed from the applicator unit after the transfer of the liquid sample. Preferably the valve element is fastened—in a form-fit and/or friction-fit manner—in the pressed-open valve unit in a further position that differs from a position of the valve element in the closed valve unit. In this way a re-closing of the valve unit, thus enabling multiple use of the transport unit which is contaminated after the first use, can be avoided in an especially advantageous manner. Alternatively, it would be conceivable that in the pressed-open valve unit the valve element is arranged loosely in the receiving region. Alternatively, it would be further conceivable that the valve unit is reclosable, wherein the valve unit could in particular be kept in the pressed-open state just by the applicator unit pressing the valve unit open actively and continuously.

It is in particular possible that the transport unit can be evacuated, such that a negative pressure relative to an ambient pressure can be set in its receiving region. For this purpose, the transport unit preferably comprises a vacuum valve unit maintaining the negative pressure in the receiving region after an evacuation. The evacuation may in particular be carried out before or during a filling in of the liquid into the receiving region. In particular, the vacuum valve unit may be configured to comprise a vacuum valve element, which closes if there a negative pressure. Preferably the vacuum valve element is configured to be opened with the evacuation and to be closed with the termination of the evacuation. Particularly preferably the vacuum valve element is configured to be kept in a closed state by the ambient pressure.

It is further proposed that the applicator unit comprises at least one blocking valve unit, which is at least configured to optionally block or release at least one of the applications of the liquid sample. This advantageously allows preventing a leaking of the liquid sample, in particular blood, at the outlet of the applicator during a filling of the channels, preferably independently from properties, in particular viscosity and surface tension. Preferably the blocking valve unit comprises at least one blocking valve, which is realized such that it can be opened and/or closed for an optional blocking or release. In particular, the first applicator element and/or the second applicator element comprises at least the blocking valve of the blocking valve unit. Preferably, viewed in a flow direction, the at least one blocking valve is arranged directly upstream of the channel exit, in particular at the end of the first flow channel and/or of the second flow channel. Particularly preferably the blocking valve, in particular the at least one blocking valve, is realized in such a way that it closes automatically when the card carrier elements fold shut.

Moreover it is proposed that the first applicator element and/or the further applicator element comprises at least one de-aeration channel for a de-aeration of at least one of the flow channels. This advantageously allows providing a discharge of air with closed blocking valves. It is also advantageously possible to provide easy flowing of the liquid sample as far as the closed valve. In particular, the de-aeration channel is configured, during an entry of the liquid sample into the first flow channel and/or the second flow channel with at least one closed blocking valve, to respectively de-aerate the first flow channel and/or the second flow channel. In particular, viewed in the flow direction, the de-aeration channel is arranged—in particular directly—upstream of the blocking valve. Especially preferentially the de-aeration channel extends at least substantially toward the channel entry, preferably towards an upper side, in particular with respect to the orientation of the sample taking device at least in the application state, in particular at least substantially parallel to a side edge of the first applicator element and/or of the second applicator element.

Beyond this a method of operating a sample taking device, in particular the aforementioned sample taking device, is proposed, wherein a liquid sample, in particular the aforementioned liquid sample, is applied to a first sample card, in particular the aforementioned first sample card, wherein the liquid sample is in an application state, in particular the aforementioned application state, applied simultaneously to a second sample card, in particular the aforementioned second sample card. This advantageously allows augmenting sampling efficiency. In particular, the sample taking device is advantageously capable of providing, in particular simultaneously, an "A" sample on the first sample card and a "B" sample on the second sample card, for example for a doping test.

The method preferably comprises a method step, in particular a fastening step, in which in particular the first sample card and the second sample card are fixed to a card carrier unit. The method preferably comprises a further method step, in particular a sampling step, which is in particular situated temporally after the fastening step and in which the liquid sample is received in the applicator unit, in particular in the first flow channel and the second flow channel. The method preferably comprises a further method step, in particular a contacting step, in which the card carrier unit is at least partly moved, in particular pivoted, relative to the applicator unit and in particular a contact of the first sample card and the second sample card with the applicator unit is established. In particular, the contacting step is situated temporally after the sampling step. Preferably the method comprises a further method step, in particular an application step, which is in particular situated temporally after the contacting step and in which the liquid sample is applied simultaneously to the first sample card and to the second sample card. The method may comprise a further method step, in particular a removal step, in which the card carrier unit is moved relative to the applicator unit and in particular the first sample card and/or the second sample card are/is removed out of the card carrier unit, for example for separate transport and/or separate storage of the first sample card and the second sample card. The removal step is in particular situated temporally after the application step.

BRIEF DESCRIPTION OF DRAWINGS

Further advantages will become apparent from the following description of the drawings. In the drawings three exemplary embodiments of the invention are illustrated. The drawings, the description and the claims contain a plurality of features in combination. Someone skilled in the art will purposefully also consider the features individually and will find further expedient combinations.

It is shown in.

DESCRIPTION OF THE EXEMPLARY EMBODIMENTS

Figure 1:
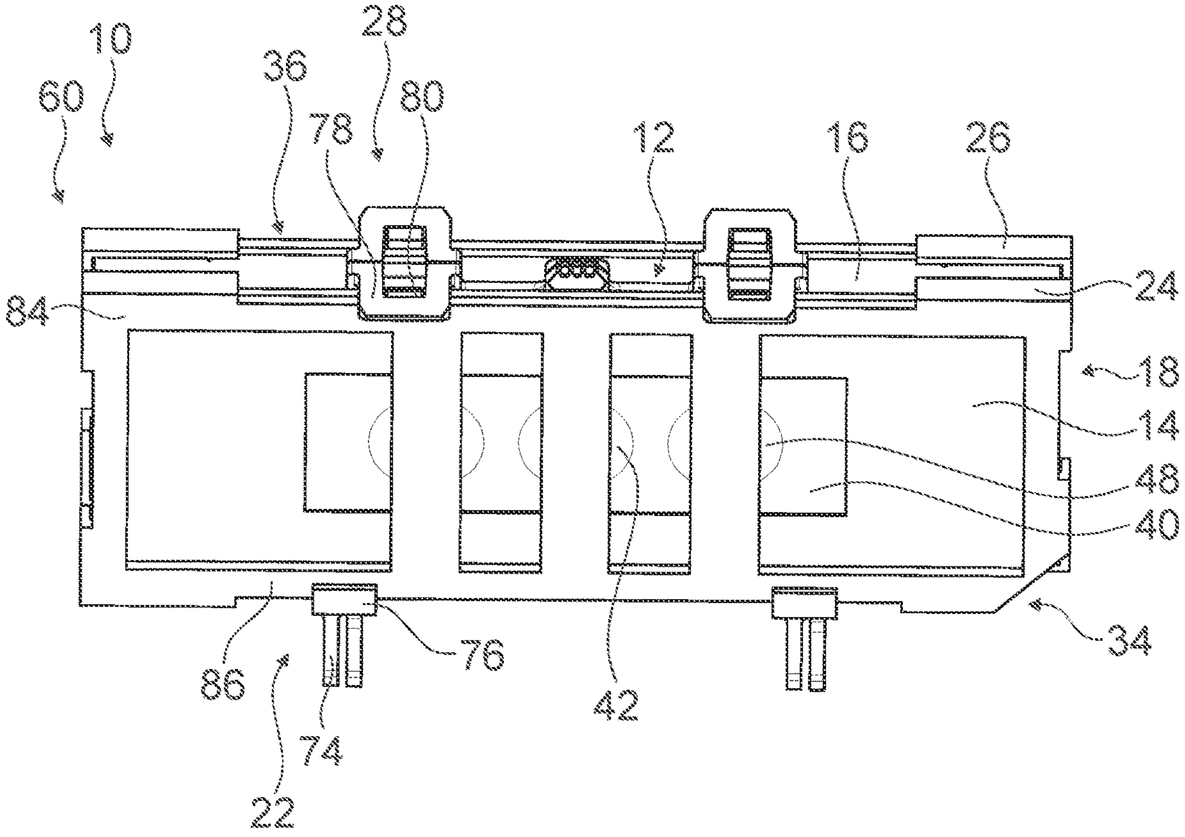
FIG. 1 a schematic illustration of a sample taking device with an applicator unit in an application state, FIG. 2 a schematic illustration of the sample taking device in a further state, FIG. 3 a schematic illustration of the applicator unit, FIG. 4 an exploded view of the applicator unit, FIG. 5 a schematic illustration of a first applicator element of the applicator unit, FIG. 6 a schematic illustration of a second applicator element of the applicator unit, FIG. 7 a flow chart for a method of operating the sample taking device, FIG. 8 a schematic illustration of an alternative exemplary embodiment of a sample taking device, with a transport unit that is separate from an applicator unit.

FIG. 1 shows a schematic illustration of a sample taking device 10 with an applicator unit 12 in an application state. The applicator unit 12 is in the application state configured for a simultaneous application of a liquid sample (not shown) to a first sample card 14 and a second sample card 16.

The applicator unit 12 is in the application state configured to create a first sample spot (not shown) on a sample carrier 40 of the first sample card 14 in a sample receiving region 48 of the sample carrier 40, which is marked here. The sample carrier 40 is configured for an absorption of the liquid sample. The sample carrier 40 is implemented of a filter paper. The sample carrier 40 comprises at least one further sample receiving region 42. The same applies correspondingly for the second sample card 16, which is realized identically to the first sample card 14.

The sample taking device 10 is part of a sample taking system 60 comprising the first sample card 14 and the second sample card 16.

The sample taking device 10 comprises a card carrier unit 18, which comprises a first holder 24 for the first sample card 14 and a second holder 26 for the second sample card 16. The first holder 24 is part of a first card carrier element 34 of the card carrier unit 18. The second holder 26 is part of a second card carrier element 36 of the card carrier unit 18. The first holder 24 and the second holder 26 are realized identically to each other. The first card carrier element 34 and the second card carrier element 36 are realized identically to each other. In the following only the first card carrier element 34 and the first holder 24 will be described, which description will correspondingly apply to the second card carrier element 36 and the second holder 26.

The first sample card 14 is fixed to the first card carrier element 34 by the first holder 24 in such a way that it is separable from the first card carrier element 34. The first card carrier element 34 comprises a card carrier plate element 84. The first sample card 14 is arranged flat on the card carrier plate element 84. The first holder 24 is in the present case formed of a section-wise overhang at a periphery of the card carrier plate element 84. The first sample card 14 is clamped within the holder 24.

The applicator unit 12 is at least in the application state connected to the card carrier unit 18. The applicator unit 12 is in the application state arranged at least partly between the first card carrier element 34 and the second card carrier element 36. The first sample card 14 is in the application state arranged at least partly between the applicator unit 12 and the first card carrier element 34. The second sample card 16 is in the application state arranged at least partly between the applicator unit 12 and the second card carrier element 36. In the application state, the applicator unit 12, the first card carrier element 34 and the second card carrier element 36 extend parallel to one another. The applicator unit 12 is in the application state arranged at least largely between the first card carrier element 34 and the second card carrier element 36.

The sample taking device 10 comprises a fixing unit 22, which prevents the applicator unit 12 from slipping out of the card carrier unit 18. The fixing unit 22 forms a form-fit connection between the applicator unit 12 and the card carrier unit 18. The fixing unit 22 comprises at least one applicator holding element 76. In the present case the fixing unit 22 comprises four identically realized applicator holding elements 76, wherein only one applicator holding element 76 is designated. The applicator unit 12 comprises the applicator holding element 76. A peripheral region 86 of the card carrier unit 18 is at least partly accommodated in the applicator holding element 76 in a form-fit manner.

Figure 2:
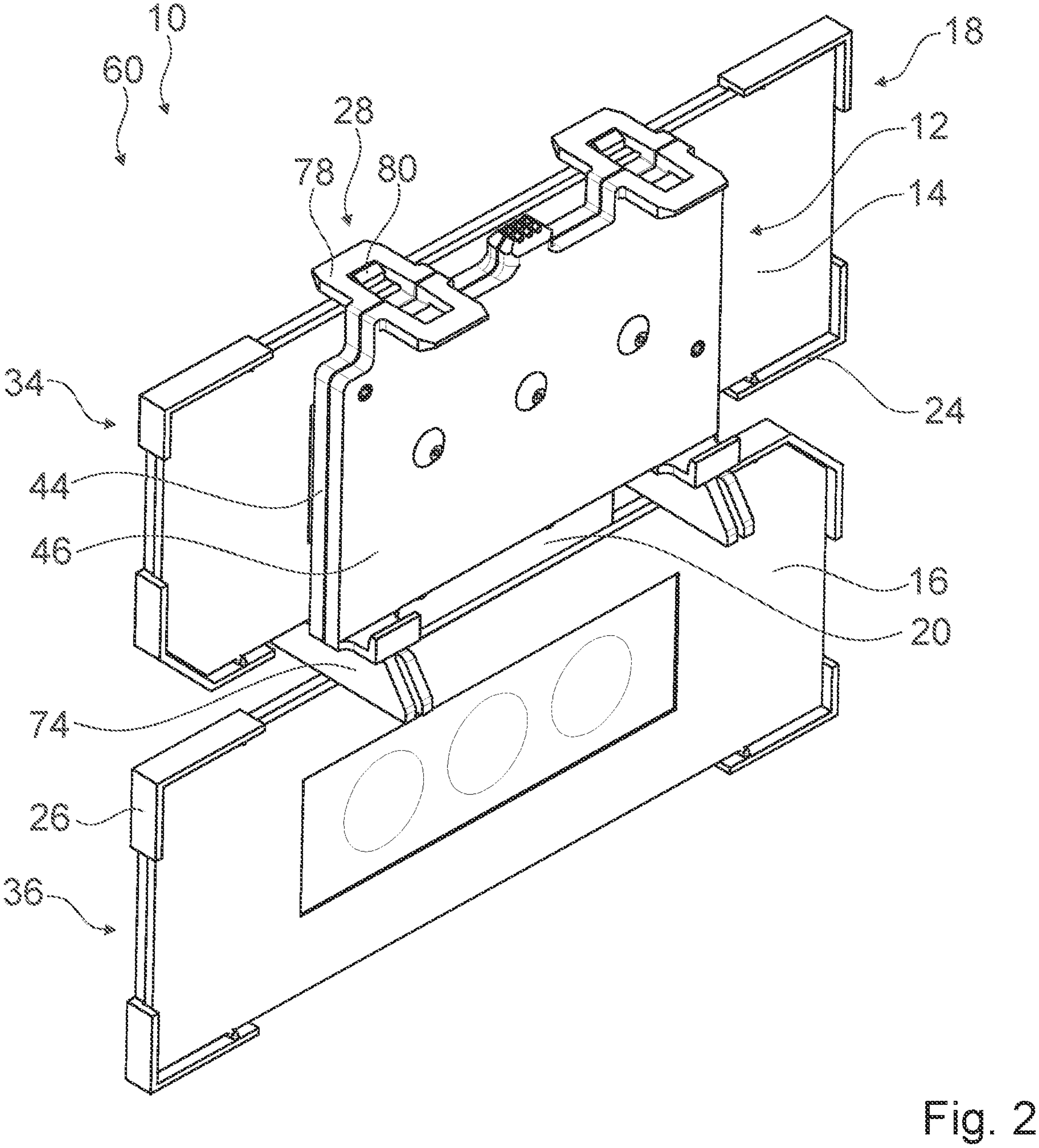

FIG. 2 shows the sample taking device 10 in a further state, which in particular differs from the application state and from a sampling state, in which the applicator unit 12 is filled with the liquid sample. The second card carrier element 36 is movable relative to the first card carrier element 34. In the present case the second card carrier element 36 is pivotable relative to the first card carrier element 34 by means of a hinge 20 of the card carrier unit 18. The first card carrier element 34 and the second card carrier element 36 are fixedly connected to each other via the hinge 20. The hinge 20 is configured for a connection of the first card carrier element 34 and the second card carrier element 36, for which an opposed arrangement of the first sample card 14 and the second sample card 16 is provided in the application state (see FIG. 1).

In the present case the first card carrier element 34 and the second card carrier element 36 are connected to each other in a one-part implementation. The first card carrier element 34 and the second card carrier element 36 are in the present case connected to each other merely by means of the hinge 20 in a one-part implementation. The hinge 20 is in the present case realized as a film hinge.

The sample taking device 10 comprises a closing unit 28, which fixes a relative position of the first card carrier element 34 with respect to the second card carrier element 36 in the application state. The closing unit 28 forms a form-fit connection between the applicator unit 12 and the card carrier unit 18. In the present case, the closing unit 28 forms a snap connection between the applicator unit 12 and the card carrier unit 18. The closing unit 28 comprises at least one closing element 78. The applicator unit 12 comprises the closing element 78. The closing unit 28 comprises at least one counter closing element 80. The card carrier unit 18 comprises the counter closing element 80. The counter closing element 80 of the card carrier unit 18 is at least in the application state accommodated at least partly in the closing element 78 in a form-fit manner (see FIG. 1). In the present case the closing unit 28 comprises four identically realized closing elements 78 and four identically realized counter closing elements 80, wherein only one closing element 78 and only one counter closing element 80 have been designated.

The applicator unit 12 is in the application state connected to the card carrier unit 18 by means of the fixing unit 22 and the closing unit 28 in an immobile manner (see FIG. 1).

Figure 3:
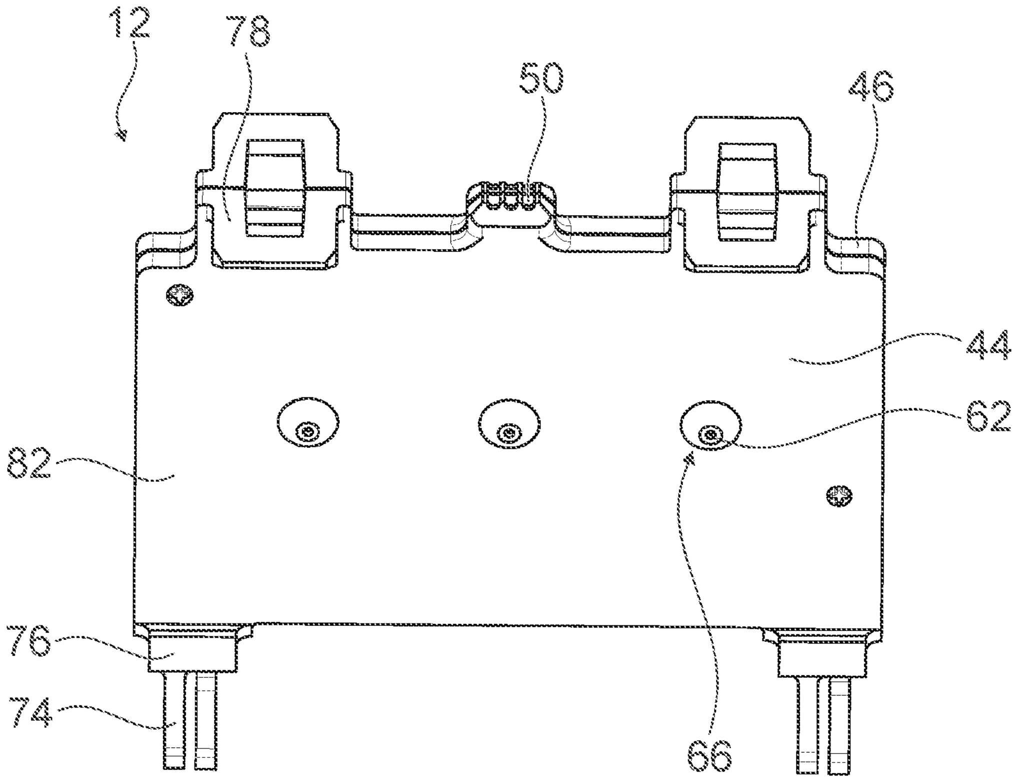

FIG. 3 shows the applicator unit 12 in an enlarged fashion. The applicator unit 12 comprises a first applicator element 44 for the application of the liquid sample to the first sample card 14, and comprises a second applicator element 46 for the application of the liquid sample to the second sample card 16. The first applicator element 44 and the second applicator element 46 are realized identically to each other. In the following only the first applicator element 44 will be described, wherein the same applies correspondingly to the second applicator element 46. The applicator element 44 comprises at least the applicator holding element 76, the closing element 78, an applicator plate element 82 and a stand base 74. In the present case the applicator unit 12 comprises four stand bases 74, wherein only one stand base 74 is designated. The sample taking device 10 is set up by means of the stand bases 74 at least in the application state (see FIG. 1).

Figure 4:
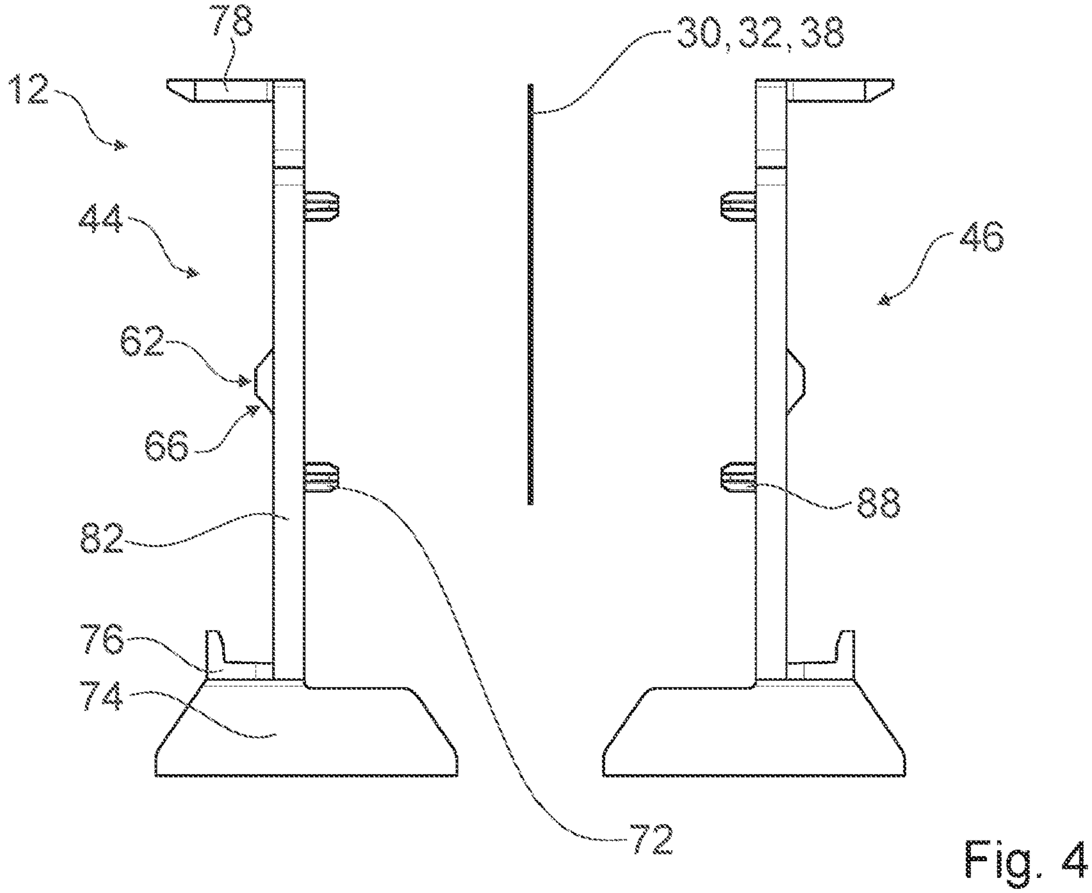

FIG. 4 shows an exploded view of the applicator unit 12. The first applicator element 44 and the second applicator element 46 are connected to each other via a separating unit 30 of the applicator unit 12. The separating unit 30 is in the present case realized as a film unit 32 with a double-gluing film 38.

Figure 5:
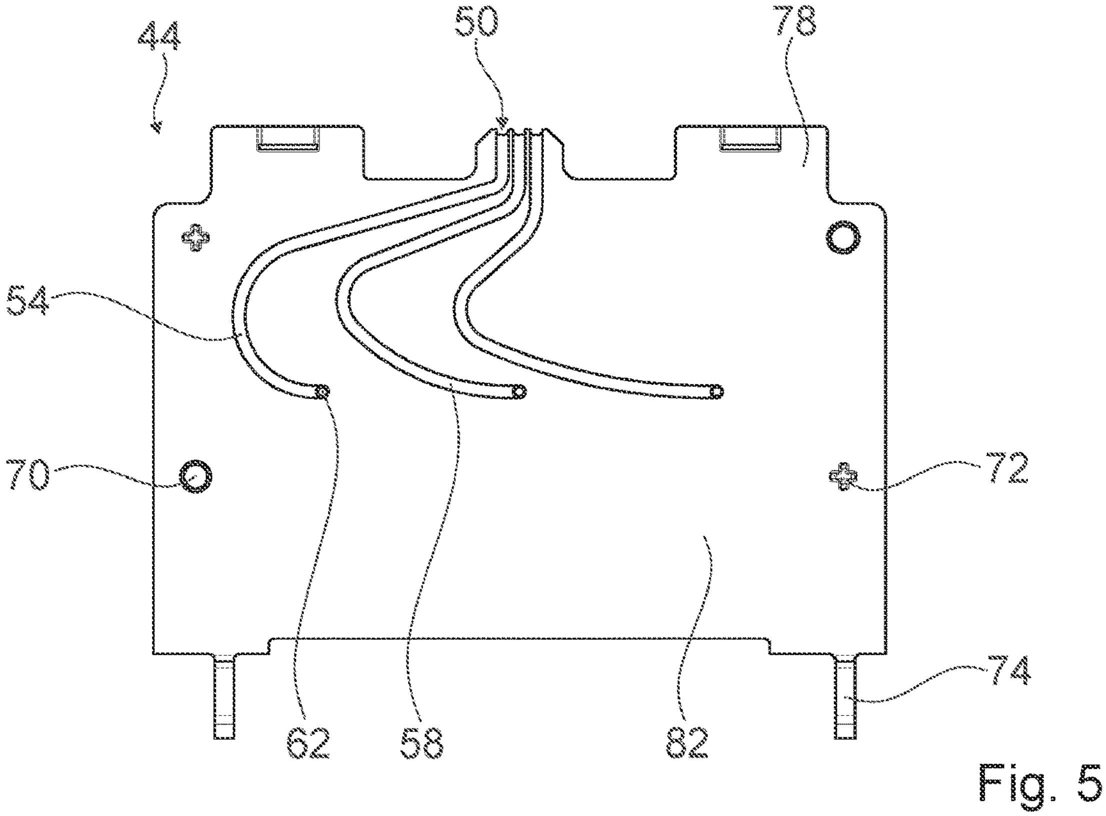

The first applicator element 44 is moreover connected to the second applicator element 46 via a plug connection (not shown). FIG. 5 shows the first applicator element 44. The first applicator element 44 comprises a plugging element 72 which is, for a friction-fit connection of the first applicator element 44 to the second applicator element 46, configured to be received in a recess 90 of the second applicator element 46 (see FIG. 6). The second applicator element 46 comprises a plugging element 88 which is, for a friction-fit connection of the first applicator element 44 to the second applicator element 46, configured to be received in a recess 70 of the first applicator element 44.

The first applicator element 44 comprises at least one first flow channel 54 and the second applicator element 46 comprises at least one second flow channel 56 (see FIG. 6), wherein the first flow channel 54 and the second flow channel 56 are at least partly closed by means of the separating unit 30 (see FIG. 4). The first flow channel 54 and the second flow channel 56 are configured for a transport of the liquid sample for the application to the first sample card 14 and to the second sample card 16. The first flow channel 54 is realized identically to the second flow channel 56. In the following only the first applicator element 44 and the first flow channel 54 will be described, wherein the same applies correspondingly for the second applicator element 46 and the second flow channel 56.

The first flow channel 54 has a channel entry 50, at which a liquid source (not shown) of the liquid sample is positioned for a filling of the first flow channel 54 with the liquid sample. The first flow channel 54 has a channel exit 62 arranged below the channel entry 50. The channel exit 62 is formed in a bulge 66 of the first applicator element 44. The bulge 66 of the first applicator element 44 is configured for a contacting of the channel exit 62 with the first sample card 14 (see FIG. 2). The first flow channel 54 is configured to accommodate a quantified volume of the liquid sample. The first flow channel 54 is realized in a curved fashion. The first applicator element 44 comprises at least one further first flow channel 58, which is capable of holding a volume of the liquid sample identical to the first flow channel 54. The further first flow channel 58 is configured to create a further sample spot (not shown) in the further sample receiving region 42 (see FIG. 1).

Figure 6:
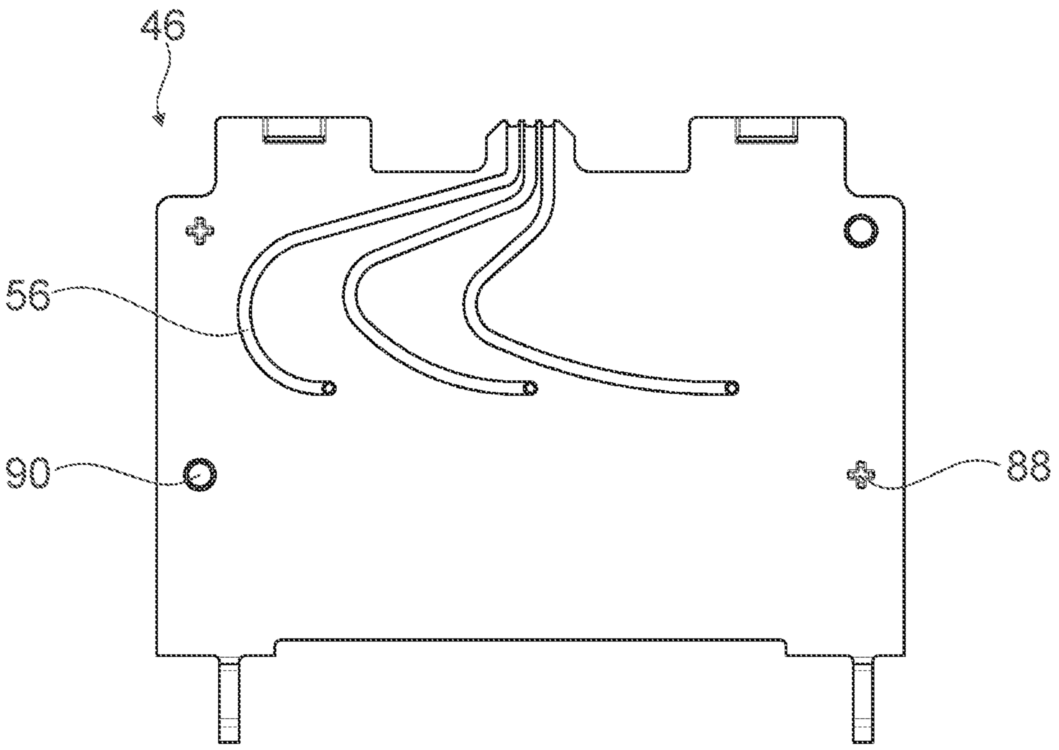

FIG. 6 shows the second applicator element 46.

Figure 7:
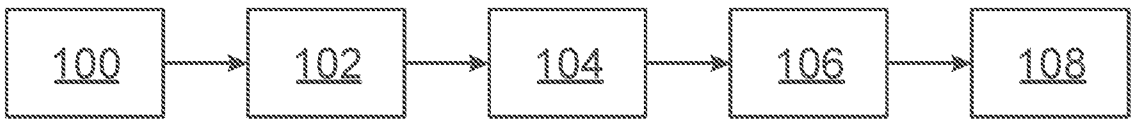

FIG. 7 shows a flow chart of a method for operating the sample taking device 10. The method comprises a fastening step 100, in which the first sample card 14 and the second sample card 16 are fixed to the card carrier unit 18. In a sampling step 102 of the method the liquid sample is received in the applicator unit 12. The method comprises a contacting step 104, in which the card carrier unit 18 is pivoted with respect to the applicator unit 12. In the contacting step 104 a respective contact of the first sample card 14 and the second sample card 16 with the applicator unit 12 is established. In an application step 106 of the method, the liquid sample is applied simultaneously to the first sample card 14 and the second sample card 16. The method comprises a removal step 108, in which the first sample card 14 and the second sample card 16 are removed out of the sample taking device 10, for example for separate transport and/or for separate storage.

In an application for the medical field, which is not part of the invention, it would be conceivable that the first applicator element 44 or the second applicator element 46 is realized as a blind plate without channels.

Two further exemplary embodiments of the invention are shown in FIGS. 8 to 11. The following description and the drawings are substantially limited to the differences between the exemplary embodiments, wherein with regard to components having the same denomination, in particular to components having the same reference numerals, principally the drawings and/or the description of the other exemplary embodiment, in particular of FIGS. 1 to 7, may be referred to. In order to distinguish between the exemplary embodiments, the letters a and b have been added to the reference numerals of the exemplary embodiments in FIGS. 8 to 11.

Figure 8:
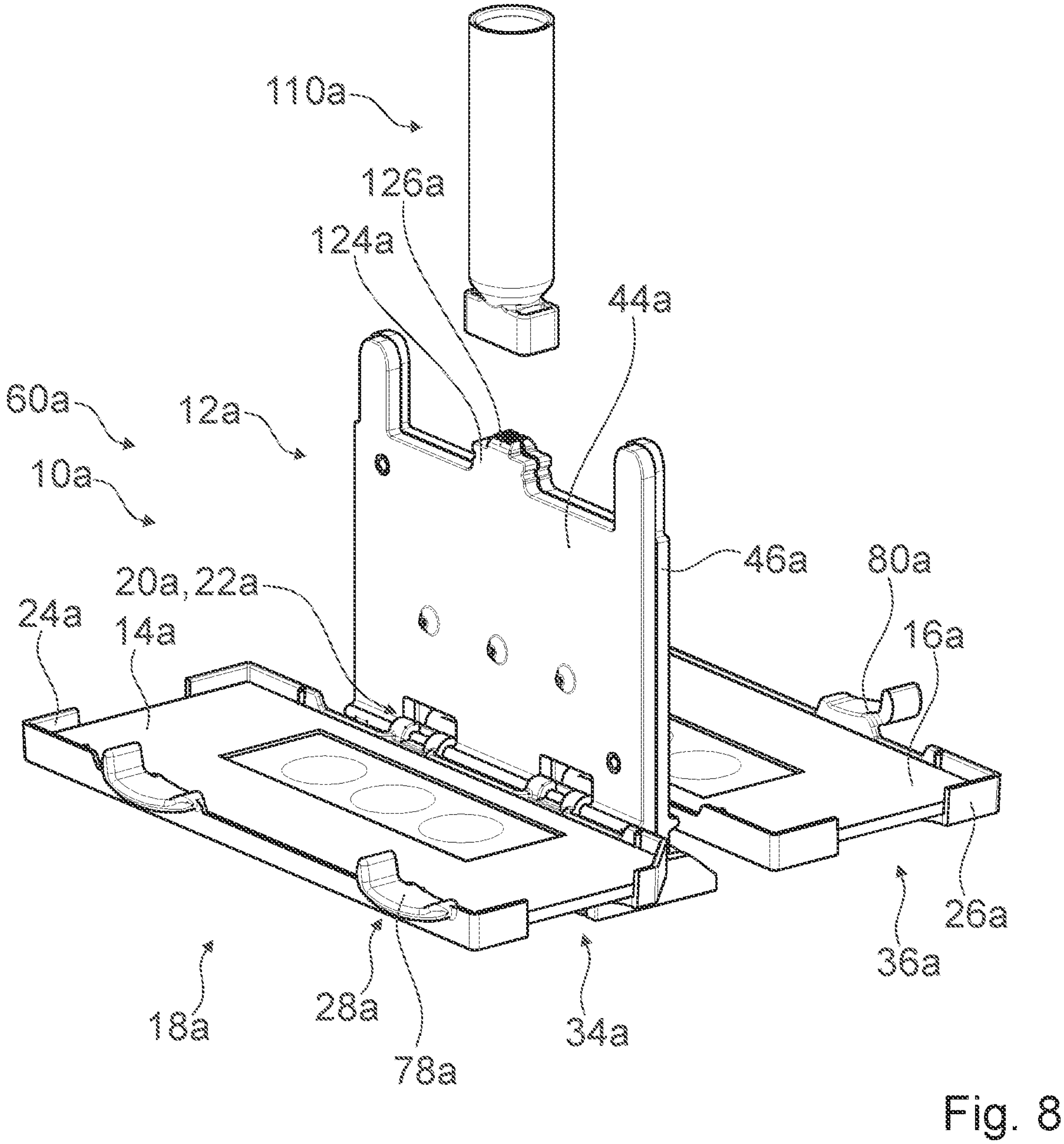

FIG. 8 shows a sample taking device 10*a* of a sample taking system 60*a*. The sample taking device 10*a* comprises a transport unit 110*a* which is, for a transfer of a liquid sample (not shown) to an applicator unit 12*a*, connectable to the applicator unit 12*a* (see FIG. 9). The transport unit 110*a* is configured for a transport of the liquid sample between a liquid source (not shown) and the applicator unit 12*a*. The transport unit 110*a* is section-wise realized in a tube-shaped manner.

A first card carrier element 34*a* is in the present case connected to a second card carrier element 36*a* via the applicator unit 12*a*. The first card carrier element 34*a* and the second card carrier element 36*a* are connected to the applicator unit 12*a* in each case via a hinge 20*a*. A fixing unit 22*a* is realized integrally with the hinge 20*a*.

The first card carrier element 34*a* comprises a closing element 78*a*. The second card carrier element 36*a* comprises a counter closing element 80*a*. A closing unit 28*a* with the closing element 78*a* and the counter closing element 80*a* is configured for a fixing of the relative position of the first card carrier element 34*a* with respect to the second card carrier element 36*a* in the application state. In the present case, the closing unit 28*a* works like a snap fit.

The applicator unit 12*a* comprises a projection 124*a*. The projection 124*a* protrudes relative to a flat upper edge of the applicator unit 12*a*. The projection 124*a* comprises an actuation element 126*a*. The actuation element 126*a* is arranged above the remaining projection 124*a*. With respect to at least one viewing direction, the actuation element 126*a* is realized narrower than the remaining projection 124*a*. The actuation element 126*a* comprises at least one channel entry (not shown).

Figure 9:
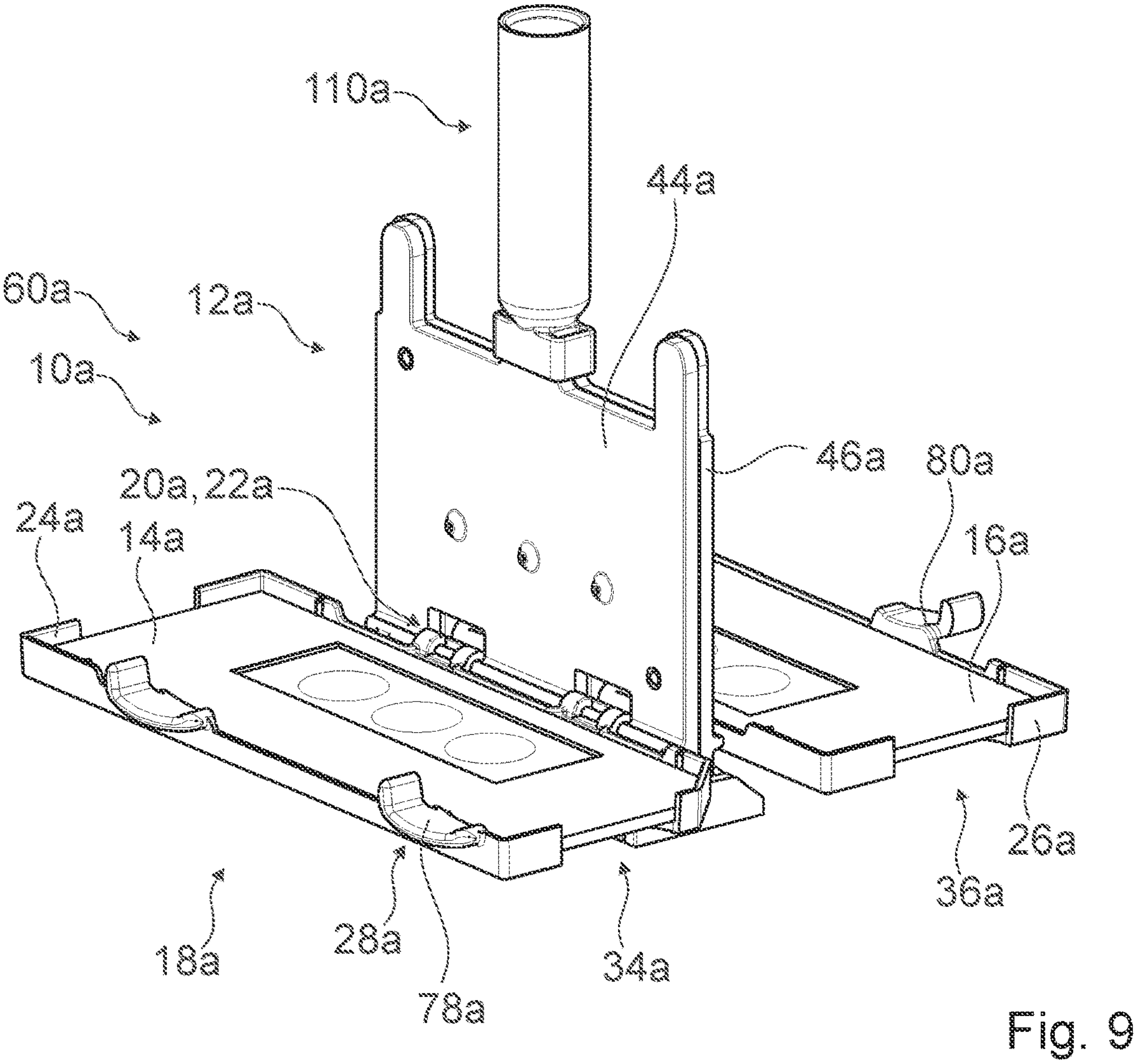
FIG. 9 a schematic illustration of the sample taking device with the transport unit that is connected to the applicator unit, FIG. 10 a sectional view of the transport unit, and FIG. 11 a schematic illustration of a further alternative exemplary embodiment of a sample taking device with an applicator unit comprising at least one blocking valve unit.

FIG. 9 shows the sample taking device 10*a* in a sampling state. The transport unit 110*a* is at least in the sampling state connected to the applicator unit 12*a*. In the sampling state, the transport unit 110*a* is connected to the applicator unit 12 in a fluid-tight fashion. The transport unit 110*a* is connectable to the applicator unit 12*a* in a form-fit and friction-fit manner. For the transfer of the liquid sample to the applicator unit 12*a*, the transport unit 110*a* is plugged onto the applicator unit 12*a* by pressing.

Figure 10:
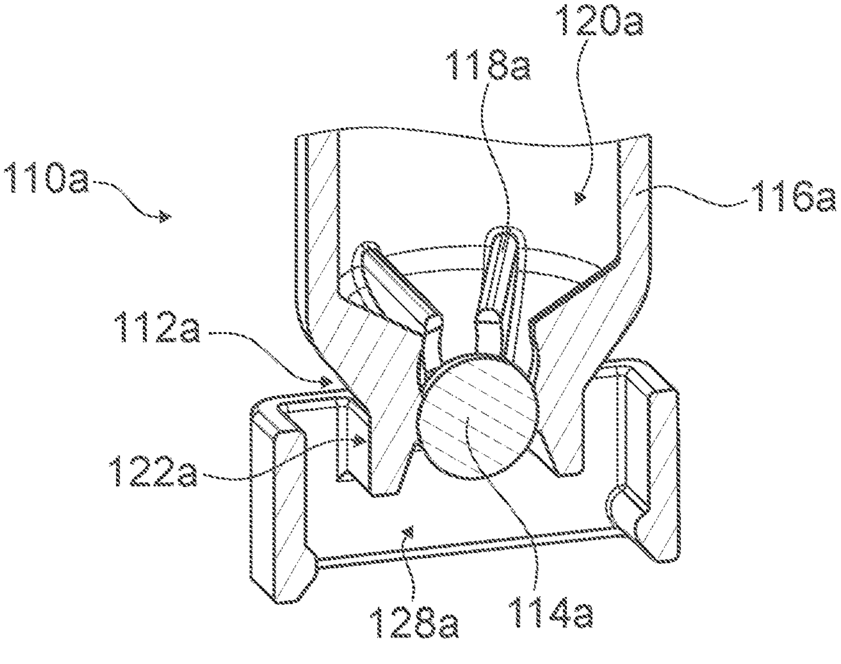

FIG. 10 shows a sectional view of the transport unit 110*a* in a state corresponding to FIG. 8. The transport unit 110*a* comprises a valve unit 112*a* which is configured, during a connection of the transport unit 110*a* to the applicator unit 12*a*, to be pressed open by the applicator unit 12*a*.

The valve unit 112*a* comprises a valve element 114*a*. The valve element 114*a* is in the present case realized as a ball made of metal. The transport unit 110*a* comprises an outer body 116*a*. The outer body 116*a* is section-wise realized in a tube-shaped manner and delimits a receiving region 120*a* for the liquid sample. The valve unit 112*a* comprises at least a portion of the outer body 116*a*.

In a closed state of the valve unit 112*a*, the valve element 114*a* is supported in a form-fit manner in a narrowing 122*a* in the outer body 116*a* of the transport unit 110*a*. The outer body 116*a* has in the present case valve bulges 118*a*, wherein only one valve bulge 118*a* is designated. The valve element 114*a* can be pressed between the valve bulges 118*a* by the applicator unit 12*a*. The liquid sample can be transferred to the applicator unit 12*a* between the valve bulges 118*a*. In the present case the valve bulge 118*a* is realized in a one-part implementation with the outer body 116*a*.

The transport unit 110*a* comprises an applicator unit receiving space 128*a* which is configured, for a transfer of the liquid sample, to accommodate a portion of the applicator unit 12*a*. For a transfer of the liquid sample, the applicator unit receiving space 128*a* is configured to receive the projection 124*a* (see FIG. 8). The applicator unit receiving space 128*a* is delimited at least partly by the outer body 116*a*. A shape of the applicator unit receiving space 128*a* corresponds at least substantially to a shape of the projection 124*a*.

The actuation element 126*a* is configured for pressing open the valve unit 112*a* for a contact to the valve element 114*a*.

Figure 11:
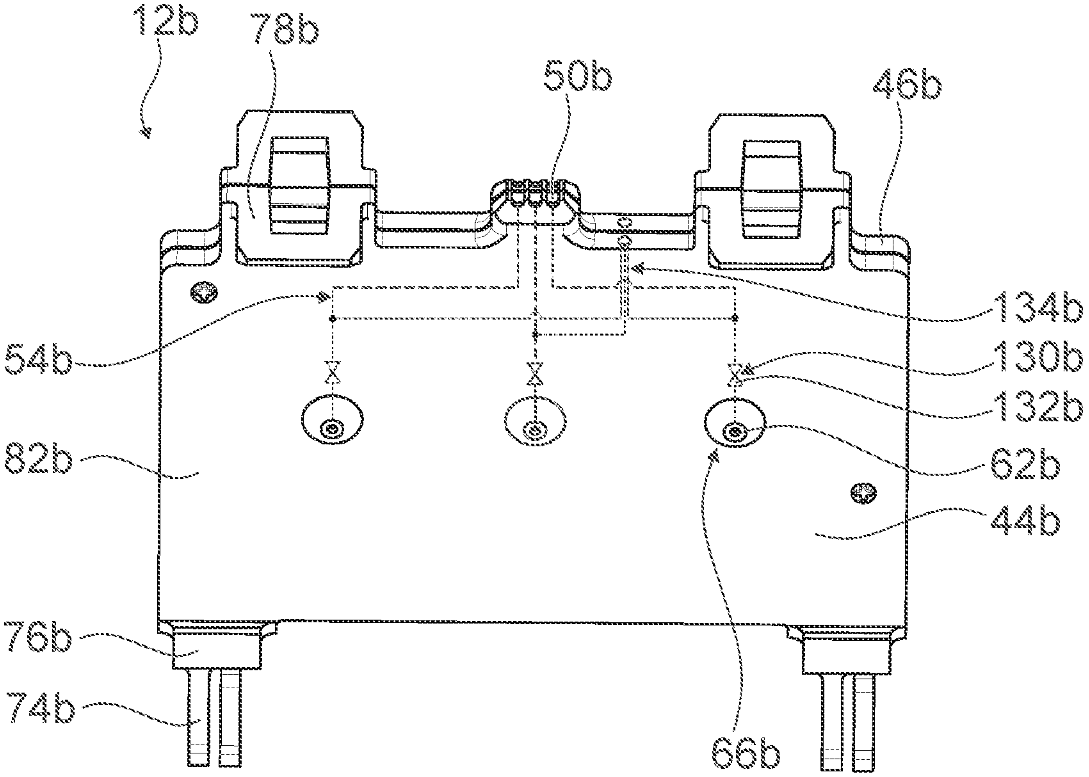

FIG. 11 shows a further sample taking device 10*b* of a sample taking system 60*b*. The sample taking device 10*b* comprises an applicator unit 12*b*. The applicator unit 12*b* comprises at least one blocking valve unit 130*b*. The blocking valve unit 130*b* is configured for optionally blocking or releasing at least one of at least two applications of a liquid sample. The blocking valve unit 130*b* comprises at least one blocking valve 132*b*. The applicator unit 12*b* comprises at least one first applicator element 44*b* and a second applicator element 46*b*. The first applicator element 44*b* and/or the second applicator element 46*b* comprises at least the blocking valve 132*b* of the blocking valve unit 130*b*. The first applicator element 44*b* and the second applicator element 46*b* in each case comprise at least one first flow channel 54*b* and at least one second flow channel 56*b*. Viewed in a flow direction, the at least one blocking valve 132*b* is arranged directly upstream of a channel exit 62*b* of the first flow channel 54*b* and/or of the second flow channel 56*b*. The at least one blocking valve 132*b* is configured to automatically close when card carrier elements 34*b*, 36*b* fold shut. Alternatively or additionally, the applicator unit 12*b* comprises at least one actuation element which opens and/or closes the blocking valve 132*b* optionally. The applicator element 132*b* comprises at least three first flow channels 54*b* and/or second flow channels 56*b*, wherein each of the flow channels 54*b*, 56*b* comprises a blocking valve 132*b* at the channel exit 62*b*.

The first applicator element 44*b* and/or the second applicator element 46*b* comprises at least one de-aeration channel 134*b*. The de-aeration channel 134*b* is configured for a de-aeration of at least one of the flow channels 54*b*, 56*b*. The de-aeration channel 134*b* is configured, during an entry of the liquid sample into the first flow channel 54*b* and/or the second flow channel 56*b* with at least one closed blocking valve 132*b*, to respectively de-aerate the first flow channel 54*b* and/or the second flow channel 56*b*. Viewed in a flow direction, the de-aeration channel 134*b* is arranged directly upstream of the blocking valve 132*b*. The de-aeration channel 134*b* extends at least substantially toward a channel entry 50*b*. The de-aeration channel 134*b* extends towards an upper side of the applicator unit 12*b* with respect to the orientation of the sample taking device 10*b* in at least one application state. The first applicator element 44*b* and/or the applicator element 46*b* comprises several de-aeration channels 134*b*, wherein each first flow channel 54*b* and/or each second flow channel 56*b* has a de-aeration channel 134*b* respectively. The de-aeration channels 134*b* converge to one de-aeration opening. Alternatively, each de-aeration channel 134*b* has its own de-aeration opening.

The invention claimed is:

1. A sample taking device with an applicator unit for an application of a liquid sample to a first sample card, wherein the applicator unit is in an application state configured for a simultaneous application of the liquid sample to a second sample card, wherein the sample taking device further comprises a card carrier unit comprising a first holder for the first sample card and a second holder for the second sample card, and wherein the card carrier unit includes a first card carrier element, which comprises the first holder, and a second card carrier element, which is movable relative to the first card carrier element and comprises the second holder.

2. The sample taking device according to claim 1, wherein the second card carrier element is pivotable relative to the first card carrier element by means of at least one hinge of the card carrier unit.

3. The sample taking device according to claim 1, wherein the first card carrier element and the second card carrier element are fixedly connected to each other, in particular in a one-part implementation.

4. The sample taking device according to claim 1, wherein the applicator unit is, at least in the application state, connected to the card carrier unit.

5. The sample taking device according to claim 4, wherein the applicator unit is in the application state arranged at least partly between the first card carrier element and the second card carrier element.

6. The sample taking device according to claim 5, further comprising a fixing unit, which prevents the applicator unit from slipping out of the card carrier unit.

7. The sample taking device according to claim 1, further comprising a closing unit, which fixes a relative position of the first card carrier element with respect to the second card carrier element in the application state.

8. The sample taking device according to claim 1, wherein the applicator unit comprises a first applicator element for an application of the liquid sample to the first sample card and a second applicator element for an application of the liquid sample to the second sample card, the first applicator element and the second applicator element being connected via a separating unit, in particular a film unit, of the applicator unit.

9. The sample taking device according to claim 8, wherein the first applicator element comprises at least one first flow channel and the second applicator element comprises at least one second flow channel, the first flow channel and the second flow channel being at least partly closed by means of the separating unit.

10. The sample taking device according to claim 8, wherein the first applicator element and the second applicator element are realized so as to be identical to each other.

11. The sample taking device according to claim 8, wherein the first applicator element and/or the second applicator element comprises at least one de-aeration channel for a de-aeration of at least one flow channel.

12. The sample taking device according to claim 1, further comprising a transport unit, which is connectable with the applicator unit for a transfer of the liquid sample to the applicator unit.

13. The sample taking device according to claim 12, wherein the transport unit comprises a valve unit, which is configured, during a connection of the transport unit to the applicator unit, to be pressed open by the applicator unit.

14. The sample taking device according to claim 1, wherein the applicator unit comprises at least one blocking valve unit, which is at least configured to optionally block or release at least one of the applications of the liquid sample.

15. A sample taking system with a sample taking device according to claim 1, with the first sample card and with the second sample card.

16. A method of operating a sample taking device, in particular according to claim 1, wherein a liquid sample is applied to a first sample card, wherein the liquid sample is in an application state applied simultaneously to a second sample card.

17. A sample taking device with an applicator unit for an application of a liquid sample to a first sample card, the sample taking device further comprising a transport unit, which is connectable with the applicator unit for a transfer of the liquid sample to the applicator unit, wherein the sample taking device further comprises a card carrier unit comprising a first holder for the first sample card and a second holder for a second sample card, and wherein the card carrier unit includes a first card carrier element, which comprises the first holder, and a second card carrier element, which is movable relative to the first card carrier element and comprises the second holder.

* * * * *